United States Patent [19]

Garth

[11] Patent Number: 5,230,698
[45] Date of Patent: Jul. 27, 1993

[54] EXTENDED WEAR CERVICAL COLLAR

[76] Inventor: Geoffrey C. Garth, 32 57th Pl., Long Beach, Calif. 90803

[21] Appl. No.: 772,876

[22] Filed: Oct. 8, 1991

Related U.S. Application Data

[63] Continuation of Ser. No. 623,853, Dec. 7, 1990, Pat. No. 5,097,824.

[51] Int. Cl.$^5$ ............................................. A61F 5/04
[52] U.S. Cl. ............................... 602/18; 128/DIG. 23
[58] Field of Search ................................. 602/17–19; 128/DIG. 23

[56] References Cited

U.S. PATENT DOCUMENTS

| | | |
|---|---|---|
| Re. 32,219 | 8/1986 | Garth . |
| 2,818,063 | 12/1957 | Smith et al. . |
| 3,285,243 | 11/1966 | Yellin ...................... 128/DIG. 23 X |
| 3,530,853 | 9/1970 | Bond . |
| 3,724,452 | 4/1973 | Nitschke ................. 128/DIG. 23 X |
| 3,916,885 | 11/1975 | Gaylord, Jr. ............ 128/DIG. 23 X |
| 4,401,111 | 8/1983 | Blackstone ............. 128/DIG. 23 X |
| 4,543,947 | 10/1985 | Blackstone ............. 128/DIG. 23 X |
| 4,708,129 | 11/1987 | Pujals, Jr. ................ 128/DIG. 23 X |
| 4,712,540 | 12/1987 | Tucker et al. . |
| 4,736,736 | 4/1988 | Moers et al. . |
| 4,827,915 | 5/1989 | Gorsen . |
| 4,886,052 | 12/1989 | Calabrese ............... 128/DIG. 23 X |
| 4,940,043 | 7/1990 | Burns et al. ............. 128/DIG. 23 X |

FOREIGN PATENT DOCUMENTS 8701028 2/1987 World Int. Prop. O. .

OTHER PUBLICATIONS

Orthopedic Equipment Co. Catalog, p. 194, 1964.

*Primary Examiner*—Richard J. Apley
*Assistant Examiner*—Linda C. M. Dvorak
*Attorney, Agent, or Firm*—Kenyon & Kenyon

[57] ABSTRACT

A cervical collar is disclosed which is formed from a stiff flexible plastic material and comprises (a) a neck encircling band comprising a back portion and a front portion and (b) a chin support formed from such plastic material. The collar provides two features which confer greater comfort when the collar is worn for extended periods of time. The chin support is supported to reduce the force of contact between the chin support and the top edge of the front portion of said collar. In a preferred embodiment, the support is provided by a plurality of load-bearing tabs extending from the top edge of the front portion of the collar. The collar also has a shelf-forming member which is attached to the back portion of the collar. Preferably the shelf-forming member is a sheet of padding material and the forming means is a strap which passes between the back portion of the collar and the shelf-forming member such that when the strap is engaged to hold the back portion in a flexed position the shelf-forming member forms the supporting shelf.

3 Claims, 15 Drawing Sheets

EXTENDED WEAR CERVICAL COLLAR

This is a continuation of application Ser. No. 07/623,853, filed Dec. 7, 1990 now U.S. Pat. No. 5,097,824.

FIELD OF THE INVENTION

The present invention relates generally to cervical collars, more particularly to cervical collars which provide cervical support while allowing comfortable extended wear.

BACKGROUND OF THE INVENTION

Recently many cervical collars have been marketed which are constructed from stiff, flexible plastic materials. These designs provide cervical support without the metal structure and bulk associated with prior collars. Thus, the collars are more portable, easily stored and relatively easy to use compared to more traditional devices. These collars include those disclosed in U.S. Reissue Pat. No. 32,219 and U.S. Pat. No. 4,712,540 and collars sold on the market by Jerome Medical, Mt. Laurel, N.J., under the trade name "NecLoc".

Applicants are inventors of the "STIFNECK" TM collar disclosed as the preferred embodiment in U.S. Reissue Pat. No. 32,219 (the disclosure of which is incorporated herein by reference as if fully set forth) which has become an industry leader. Although the STIFNECK collar provides superior cervical support and is easy to use in an emergency situation where strict immobilization is the key and patient comfort is not a primary concern, it has only limited use as an extended wear collar (i.e., a collar for patient wear over a treatment period, usually days or weeks) where immobilization concerns are much less strict and patient comfort is of much greater concern. This is also true for the collar of U.S. Pat. No. 4,712,540 and the NecLoc collar. It would, therefore, be desirable to provide a cervical collar which provides the portability and convenience of these types of collars, while providing features which confer greater patient comfort.

SUMMARY OF THE INVENTION

A cervical collar is disclosed which is formed from a stiff flexible plastic material and comprises (a) a neck encircling band comprising a back portion and a front portion and (b) a chin support formed from such plastic material. The collar provides two features which confer greater comfort when the collar is worn for extended periods of time. The chin support is supported by load-bearing means which redistributes the force of contact between the chin support and the top edge of the front portion of the collar. In a preferred embodiment, the load bearing means is a plurality of load-bearing tabs extending from the top edge of the front portion of the collar. The collar also has a shelf-forming member which is attached to the back portion of the collar. Forming means are also attached to the back portion of the collar for holding the back portion in a flexed conformation and for forming an supporting shelf from the shelf-forming member. Preferably the shelf-forming member is a sheet of padding material and the forming means is a strap which passes between the back portion of the collar and the shelf-forming member such that when the strap is engaged to hold the back portion in a flexed position the shelf-forming member forms the supporting shelf.

BRIEF DESCRIPTION OF THE FIGURES

In FIG. 6, the padding shown in FIG. 5 has been removed to show the underlying structure of the depicted embodiment.

DETAILED DESCRIPTION OF THE PREFERRED EMBODIMENT

Figure 1:
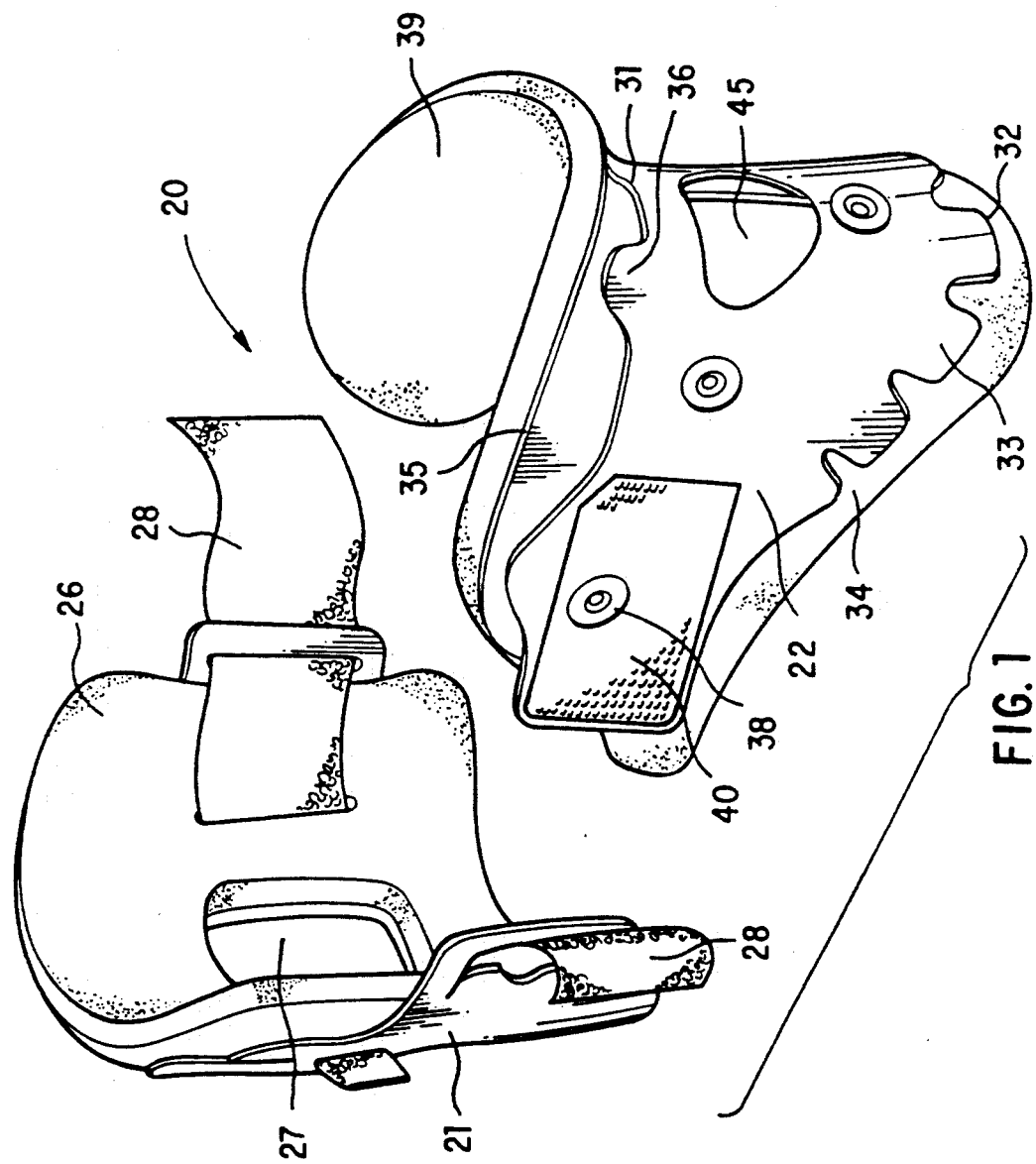
FIG. 1 is a perspective view of a preferred embodiment of the collar of the present invention.
Figure 2:
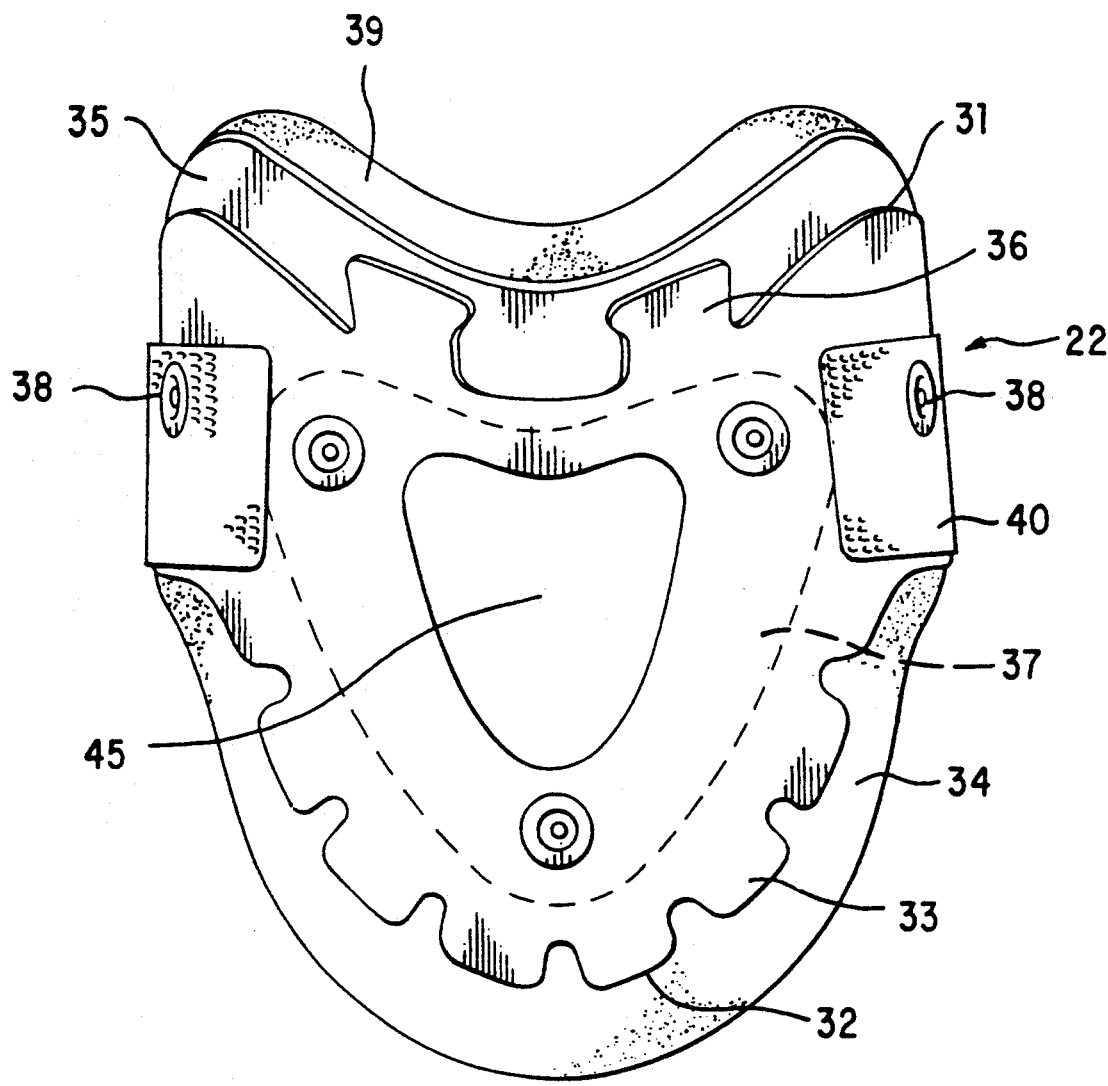
FIGS. 2 and 3 are, respectively, front and back plan views of the front portion of a preferred embodiment of the present invention.
Figure 3:
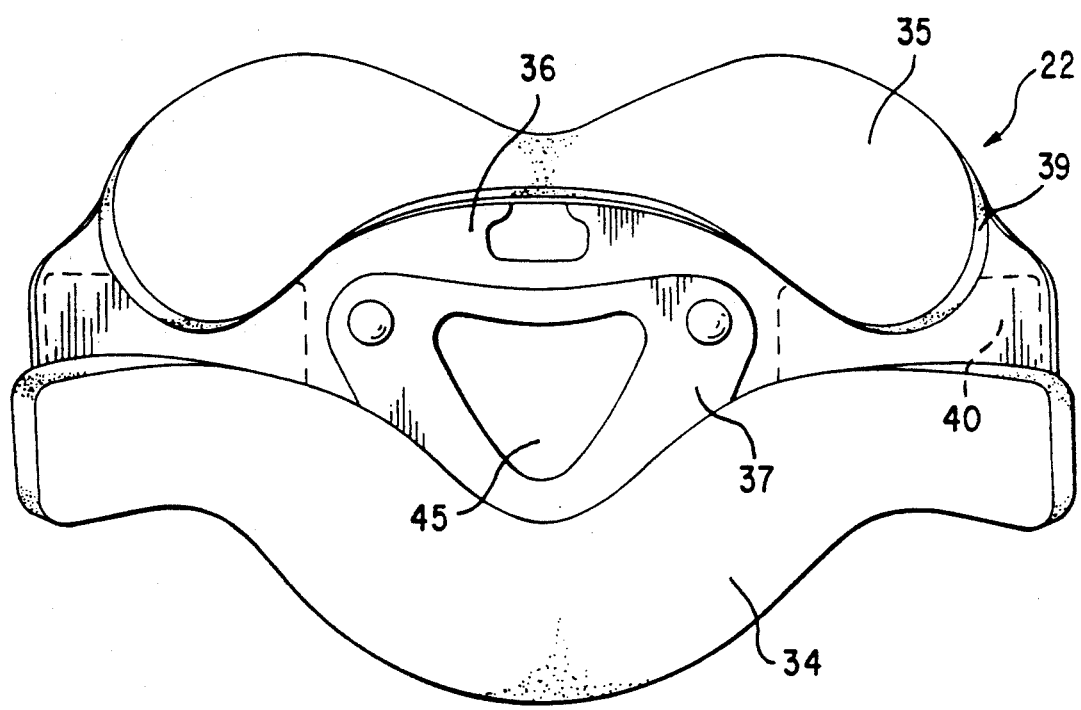
Figure 4:
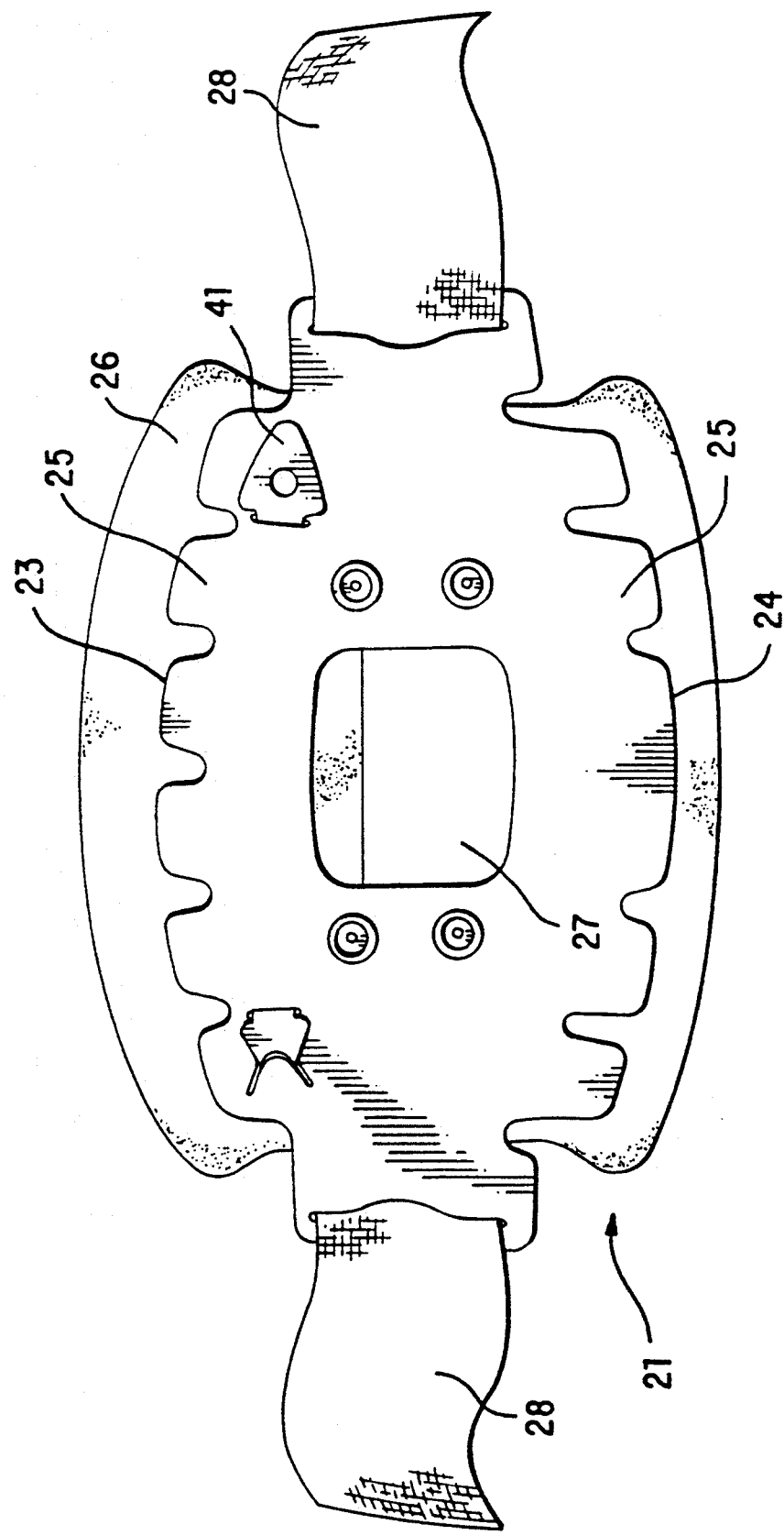
FIG. 4 is a back plan view of the back portion of a preferred embodiment of the present invention.
Figure 5:
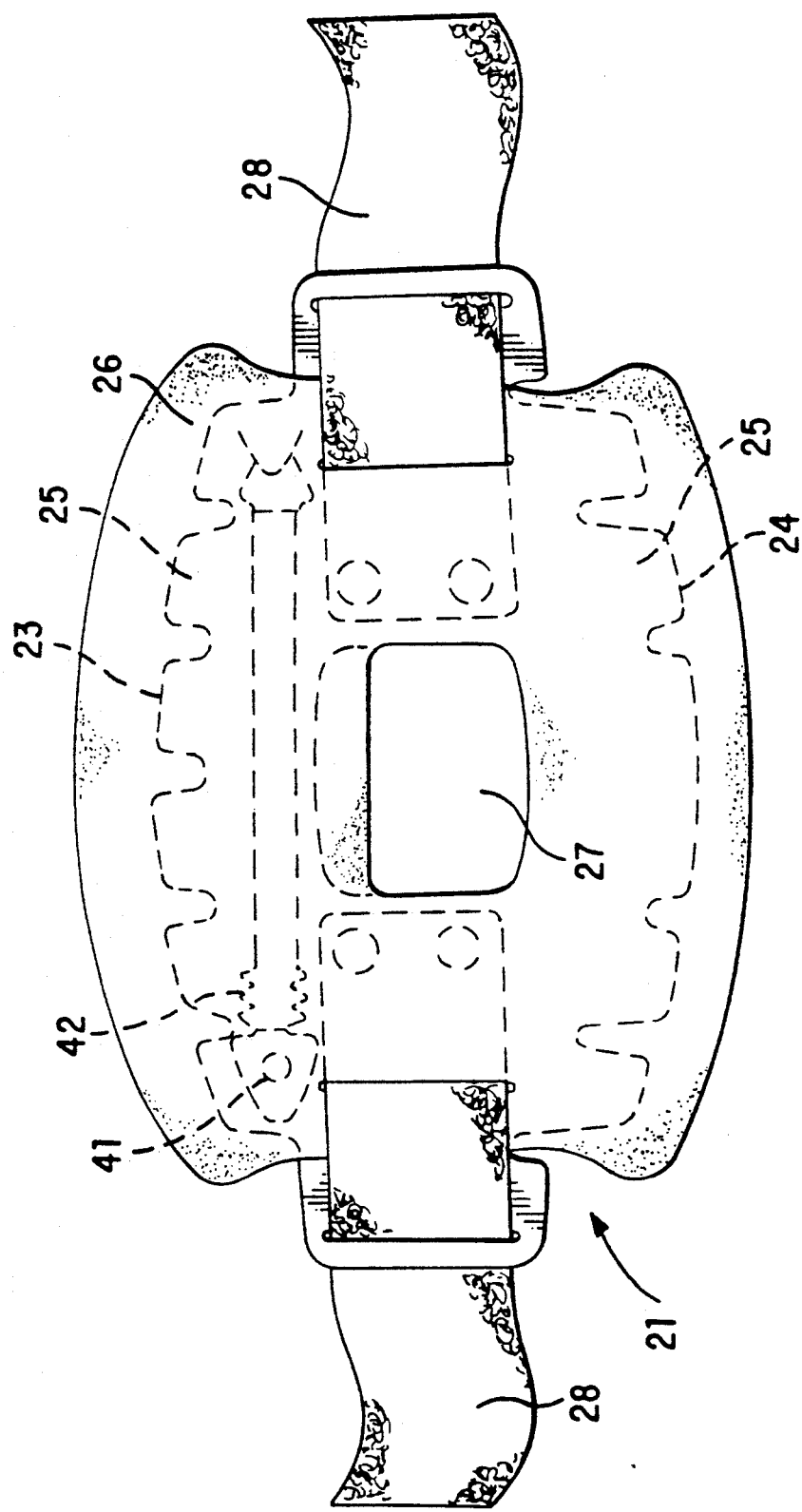
FIGS. 5 and 6 are front plan views of the back portion of a preferred embodiment of the present invention.
Figure 6:
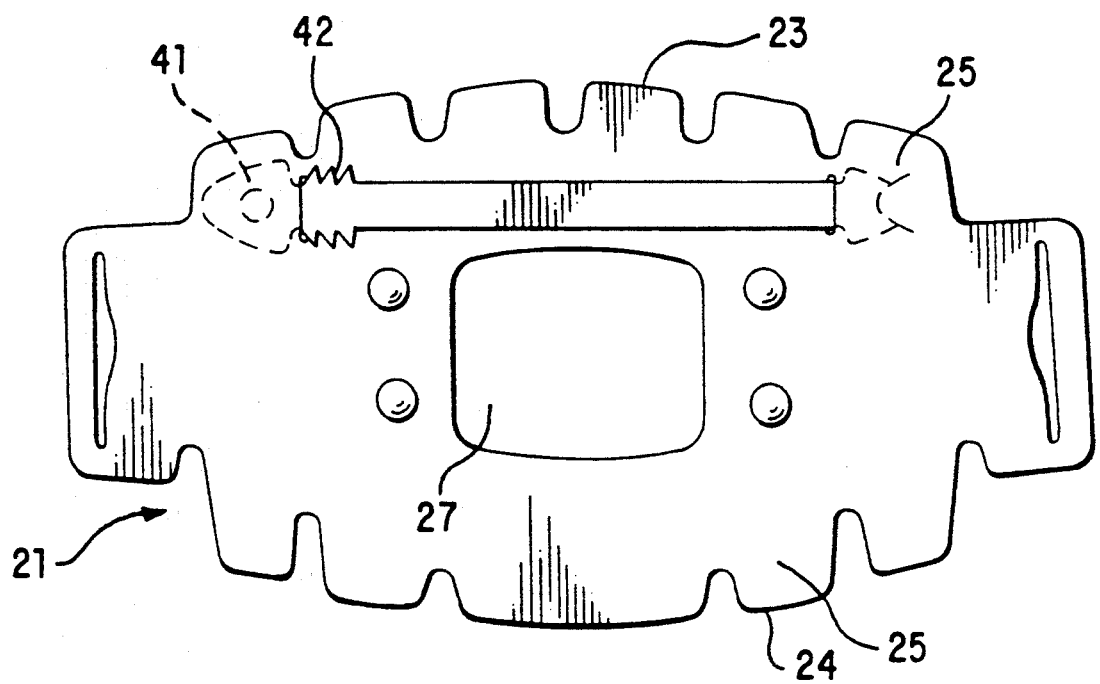
Figure 9:
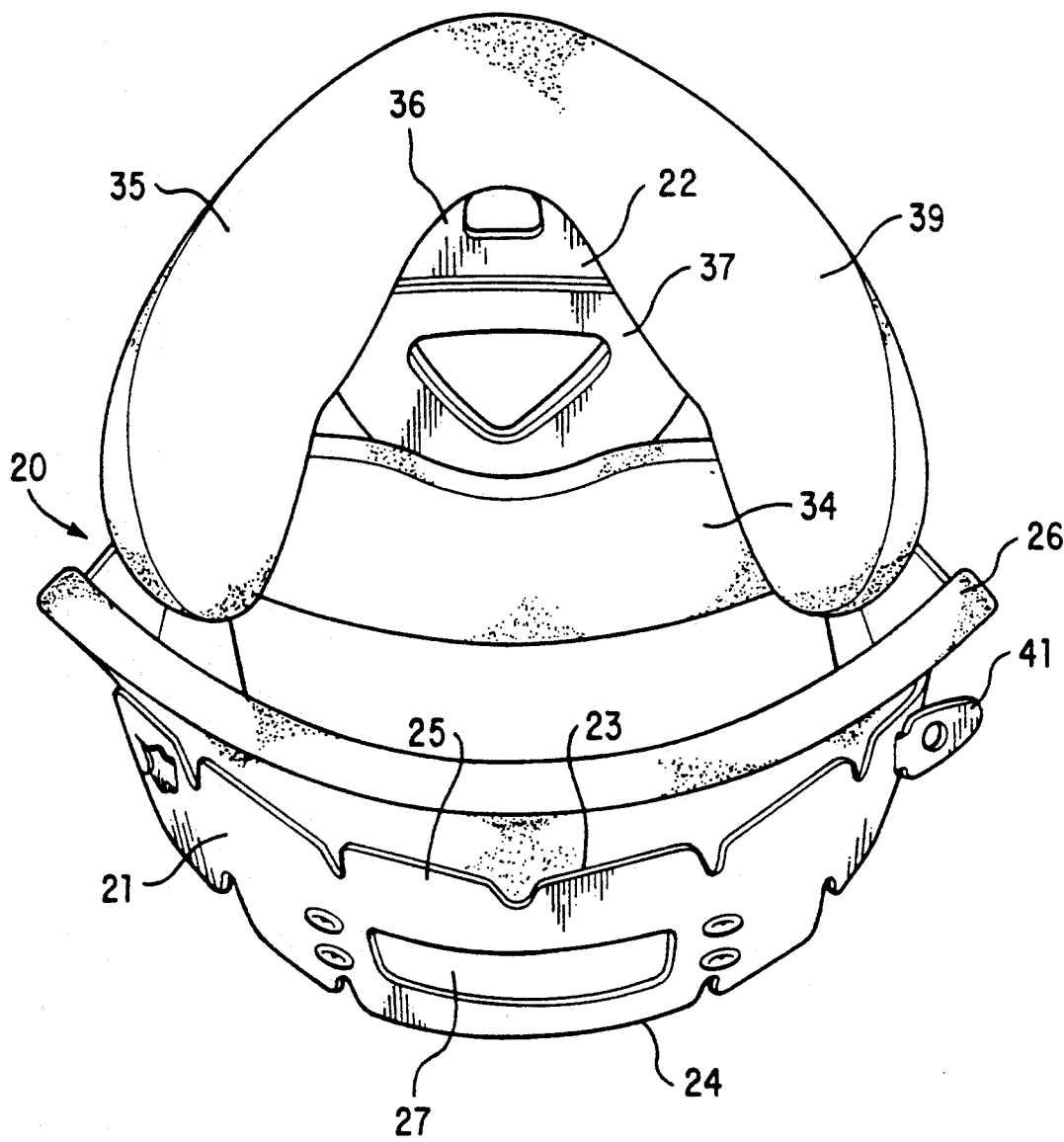
FIGS. 9 and 10 are top perspective views of two different conformations of a preferred embodiment of the present invention.
Figure 10:
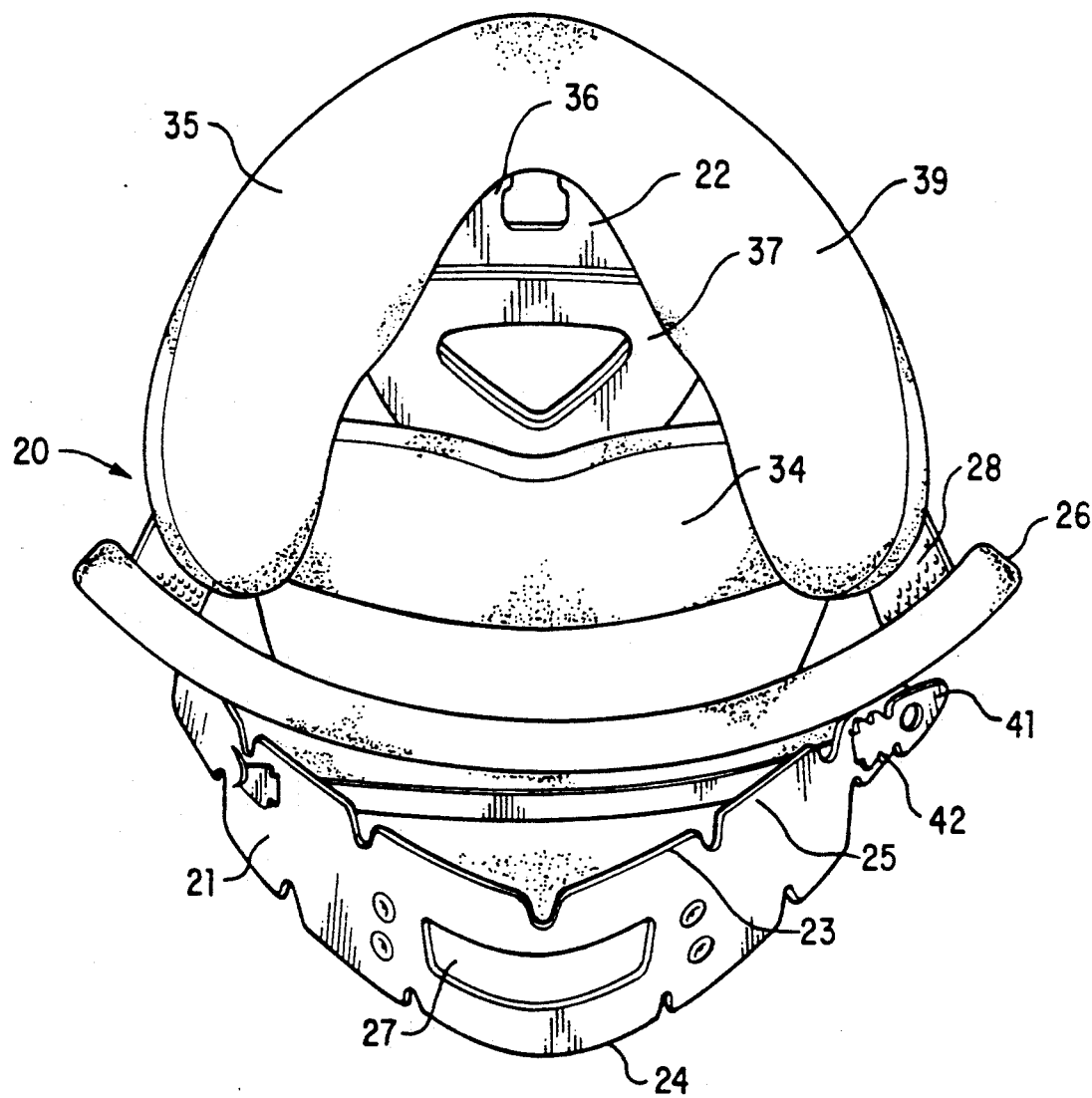

FIGS. 1-7 and 9-14 depict a preferred embodiment collar incorporating the features of the present invention. Generally, in its assembled shape, collar 20 forms a circular or ovoid configuration for surrounding the neck as shown in FIGS. 9 and 10. As shown in FIG. 1, a neck encircling band is formed from back portion 21 and front portion 22.

Back portion 21 has top 23 and bottom 24 edges which contact the wearer's body for lending support. Top edge 23 contacts the occipital region of the head and bottom edge 24 contacts the wearer's shoulders such that the head is for the most part prevented from tilting backward. A plurality of flaps 25 along edges 23 and 24 help to conform those edges to the shape of a specific wearer's head and shoulders. Back portion 21 is fitted with pad 26 which prevents edges 23 and 24 from directly contacting the wearer, thus affording greater comfort. Back portion 21 optionally has a manifold 27 which facilitates airflow through the collar. Fastening straps 28 extend from back portion 21 and are made from hook and loop fastener material, such as Velcro ®.

Back portion 21 is also fitted with means for adjusting the contour of back portion 21 and pad 26. In the embodiment shown in FIGS. 4, 6 and 7, strap 41 is fitted with notches 42 which engage with slots in back portion 21 through which strap 41 extends to hold the back portion in its flexed conformation. In the embodiment shown in FIG. 8, hook and loop strap 29 extends through slots in back portion 21 such that they are engageable with patches (not shown; attached to the surface of the back portion of the collar) which are made from hook and loop fastener material which is the mate to strap 29. Either strap 29 or strap 41 extends between pad 26 and back portion 21 as shown in the Figures. Use of strap 29 or 41 to adjust the contour of back portion 21 and pad 26 is further described below.

Front portion 22 has top 31 and bottom 32 edges. Bottom edge 32 conforms generally to the contour of the wearer's shoulders and clavicle. Flaps 33 bend to facilitate conforming bottom edge 32 to such shape. Pad 34 is optionally provided to make contact between the wearer and bottom edge 32 more comfortable. Top edge 31 is generally curved to receive chin support 35 and forms loadbearing tabs 36, which support chin support 35. The interaction of chin support 35, load-bearing tabs 36 and the top edge 31 of front portion 22 are described further below. Contact between the wearer's mandible and chin support 35 and the wearer's shoulders/clavicle and the bottom edge 32 of front portion 22 prevent significant tilting of the head forward. Fastening strips 40 (which are the mates to fastening straps 28) are provided for attaching the front and back portions of the collar as described below. Front portion 22 may also optionally have a tracheal orifice 45 which contributes to airflow through the collar and allows access to the trachea during use. Front portion 22 may also optionally be fitted with a reinforcing member 37 which lends increased rigidity and support.

In its unflexed conformation, chin support 35 is generally C-shaped. In its flexed conformation, chin support 35 is generally U- or V-shaped such that it conforms to the shape of the lower edge of the wearer's mandible (i.e., along the jaw/chin line). The ends of chin support 35 are attached to front portion 22 by fasteners 38 in the embodiment shown in the Figures. Other means for fastening the ends can be used. The ends of the chin support may be either attached to or detachable from the neck encircling band. Chin support 35 is optionally provided with pad 39 for greater comfort.

In certain alternative embodiments, the neck encircling band is formed from a single panel (for example as shown in the Figures of U.S. Reissue Pat. No. 32,219), wherein the single panel has back and front portions having features corresponding to those described herein for back portion 21 and front portion 22. In such embodiments, only one fastening strap and fastening strip is required.

In other alternative embodiments, the neck encircling band is formed from a single panel which splits in the back in a manner similar to that shown in the Figures of U.S. Pat. No. 3,530,853, wherein the single panel has back and front portions having features corresponding to those described for back portion 21 and front portion 22. In such embodiments, only one fastening strap and fastening strip is required.

The neck encircling band of collars of the present invention can be made from various stiff flexible plastics, including without limitation high and low density polyethylene, polyvinylchloride, acrylonitrile-butadiene-styrene copolymer, polypropylene, etc. Padding, straps and strips can be joined to the collar by any suitable fastening means, including without limitation snap fasteners, staples and adhesive. Although hook and loop fastening material is used as the preferred means to hold the collar in its neck encircling conformation, other means can be used to perform the same function, such as straps, buckles, snaps, fasteners, cords, tabbed strips or any other substantially nonstretch material with latching means.

Figure 11:
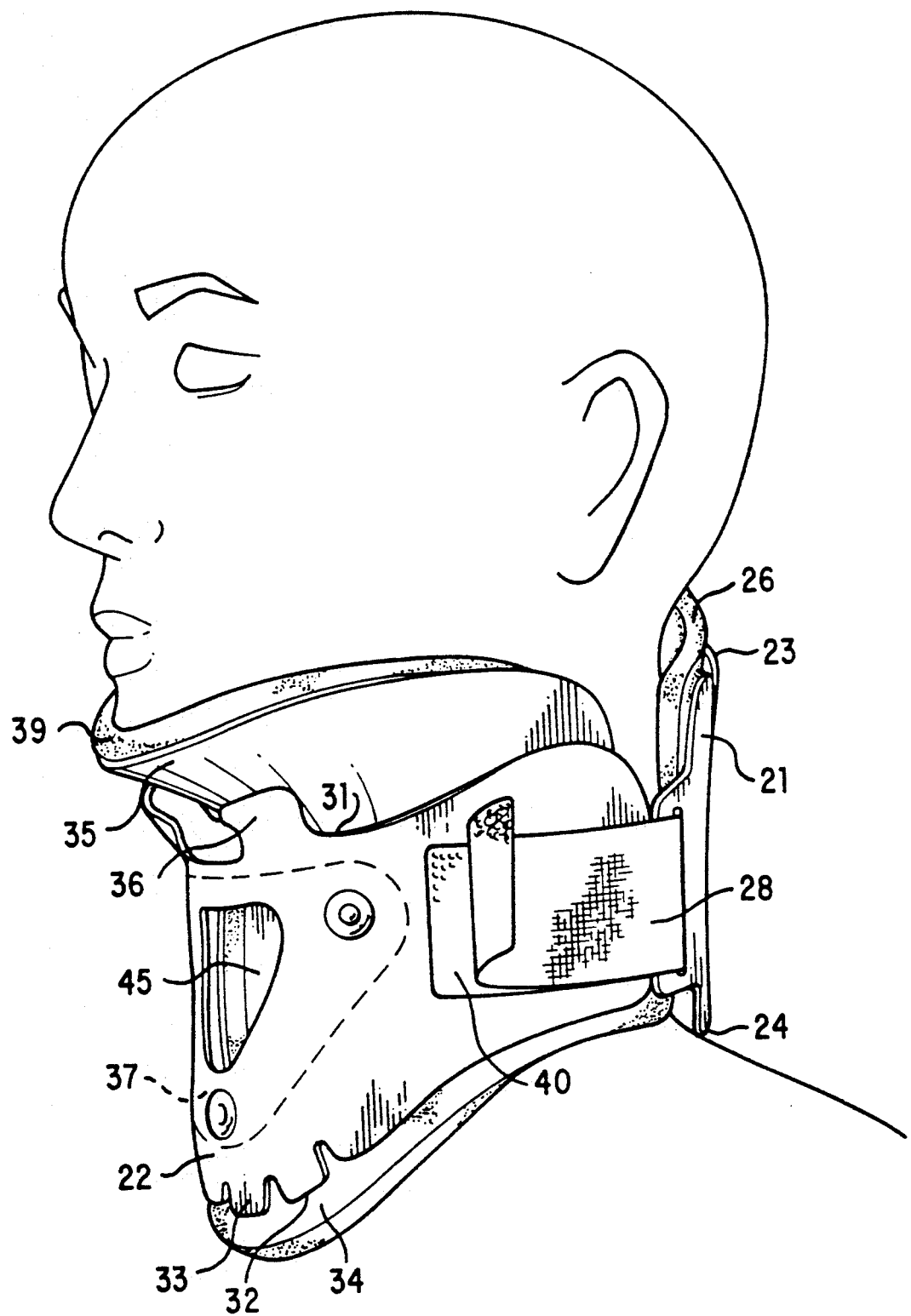
FIGS. 11-14 depict a preferred embodiment of the present invention applied to a patient.
Figure 12:
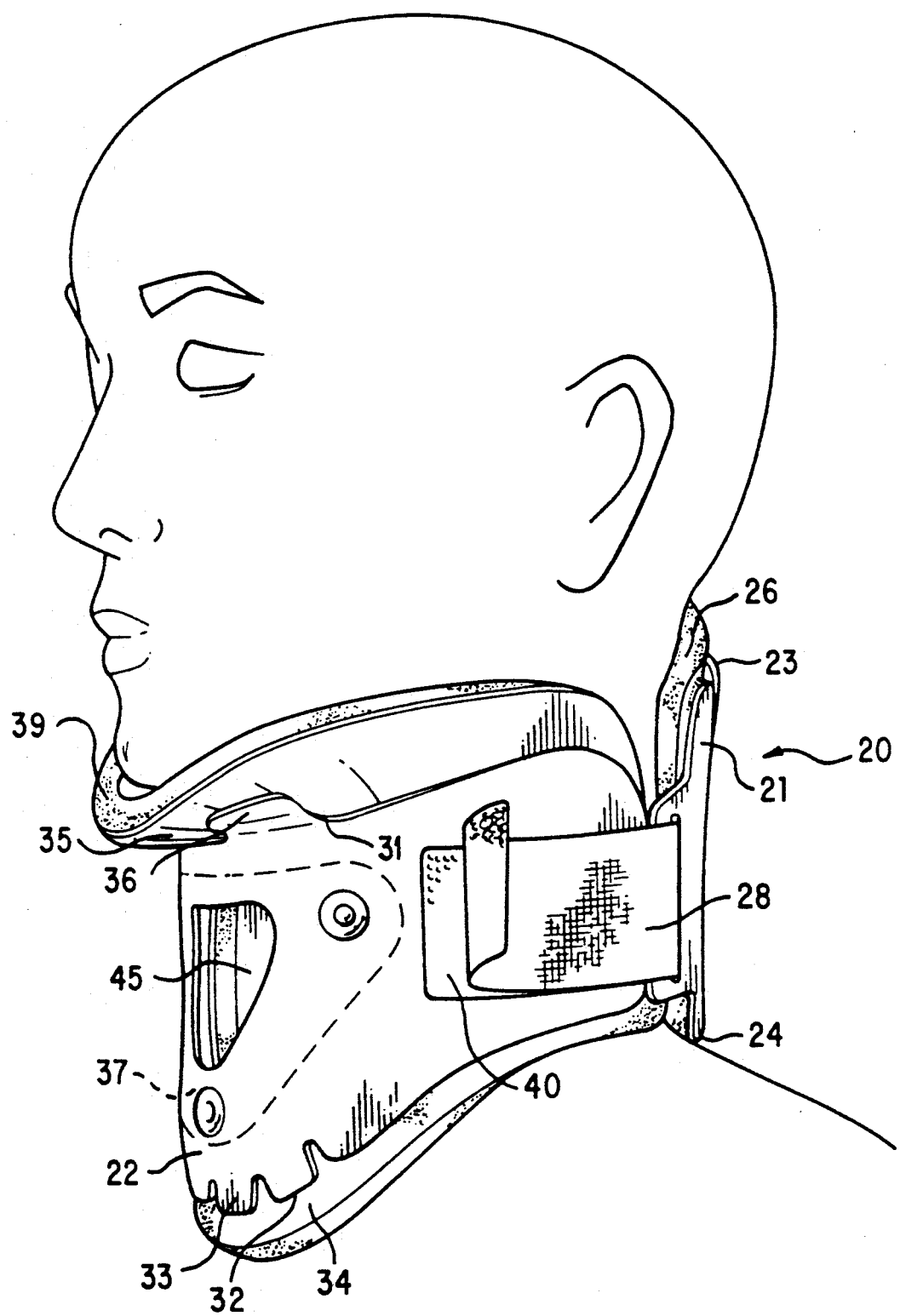

The preferred embodiment is applied to a patient as shown in FIGS. 11 and 12 as follows. Back 21 and front 22 portions and chin support 35 are positioned with respect to the wearer's head, chin, neck and shoulders. Fastening straps 28 and fastening strips 40 are engaged to secure the collar snugly around the neck in the neck encircling conformation such that flexion, extension and lateral movement of the cervical spine is restrained to the desired degree.

With prior art collars, such as that shown in U.S. Reissue Pat. No. 32,219 and U.S. Pat. No. 4,712,540, the wearer's chin bears a weight load to prevent the cervical spine from flexing (i.e., the head from tilting forward). The majority of this load is borne along the lower and lingual (inside) edge of the mandible along the line where the chin support contacts the top edge of the front portion of the collar, such as shown in certain figures of U.S. Reissue Pat. No. 32,219 and U.S. Pat. No. 4,712,540. While contact at this point is desirable for achieving strict immobilization of the spine, it can cause significant discomfort for the wearer, especially upon extended wear. Pressure from the weight load can cause pressure sores and accompanying tissue damage. Former collars also tend to concentrate a significant amount of the load underneath the patient's chin in the midline area.

Collars of the present invention provide greater wearer comfort by at least partially alleviating this load bearing problem while maintaining the desired degree of immobilization of the cervical spine. As shown in FIGS. 11 and 12, in accordance with the present invention, chin support 35 is supported at least in part by load-bearing tabs 36 rather than by top edge 31 alone. This allows the formation of points of support that move in response to an increased load on the chin support, which tends to redistribute some of the weight load from the lingual surface of the jaw to the buccal (outside) edge of the mandible, resulting in less stress at a single position. As more load is placed on the chin support, the tabs flex outwardly and the point of contact with the chin support moves toward the outer edge of the chin support (compare FIGS. 11 and 12). The flexibility of tabs 36 also allows some movement of the jaw, such that the wearer can relieve discomfort felt in a given position without losing a significant degree of immobilization. Although the load redistribution achieved by the present invention may not completely alleviate pressure sores and discomfort, such adverse effects are greatly reduced by this feature. In addition, unless fully loaded such that the tabs have flexed to the point where the load is being carried on the edge of the encircling band, little or no pressure is applied to the underside of the patient's chin in the midline area which significantly impacts patient comfort, especially while swallowing.

Collars of the present invention also provide greater wearer comfort by providing an adjustable support for the lower occipital region of the wearer's head. In prior art collars, the back of the head is supported and extension of the cervical spine is limited by contact between the bottom edge of the back portion of the collar and the wearer's shoulders and between the top edge of the back portion of the collar and a contact line on the back of the wearer's head as shown in U.S. Reissue Pat. No. 32,219 and U.S. Pat. No. 4,712,540. Although such collars provide support to the back of the head, such support is provided by contact along a single line corresponding to the line of contact of the occiput with the top edge of the collar. Collars of the present invention are fitted with means for adjusting the conformation of the back portion of the collar and its associated pad to form a shelf which provides support over a greater portion of the lower occipital region, thus reducing the more localized pressure found in former collars.

Figure 7:
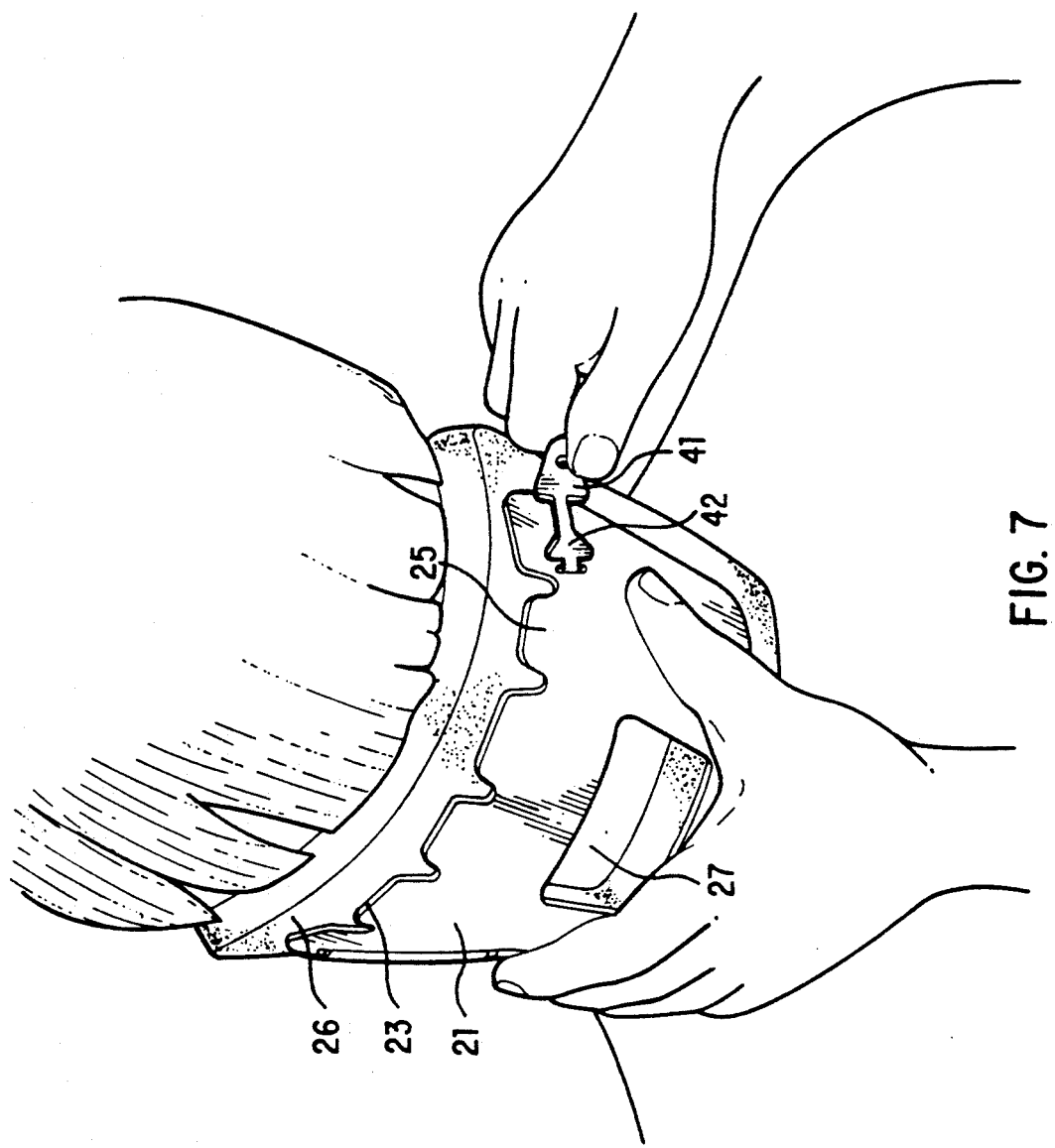
FIG. 7 depicts the application of a preferred embodiment of the present invention to a patient.
Figure 8:
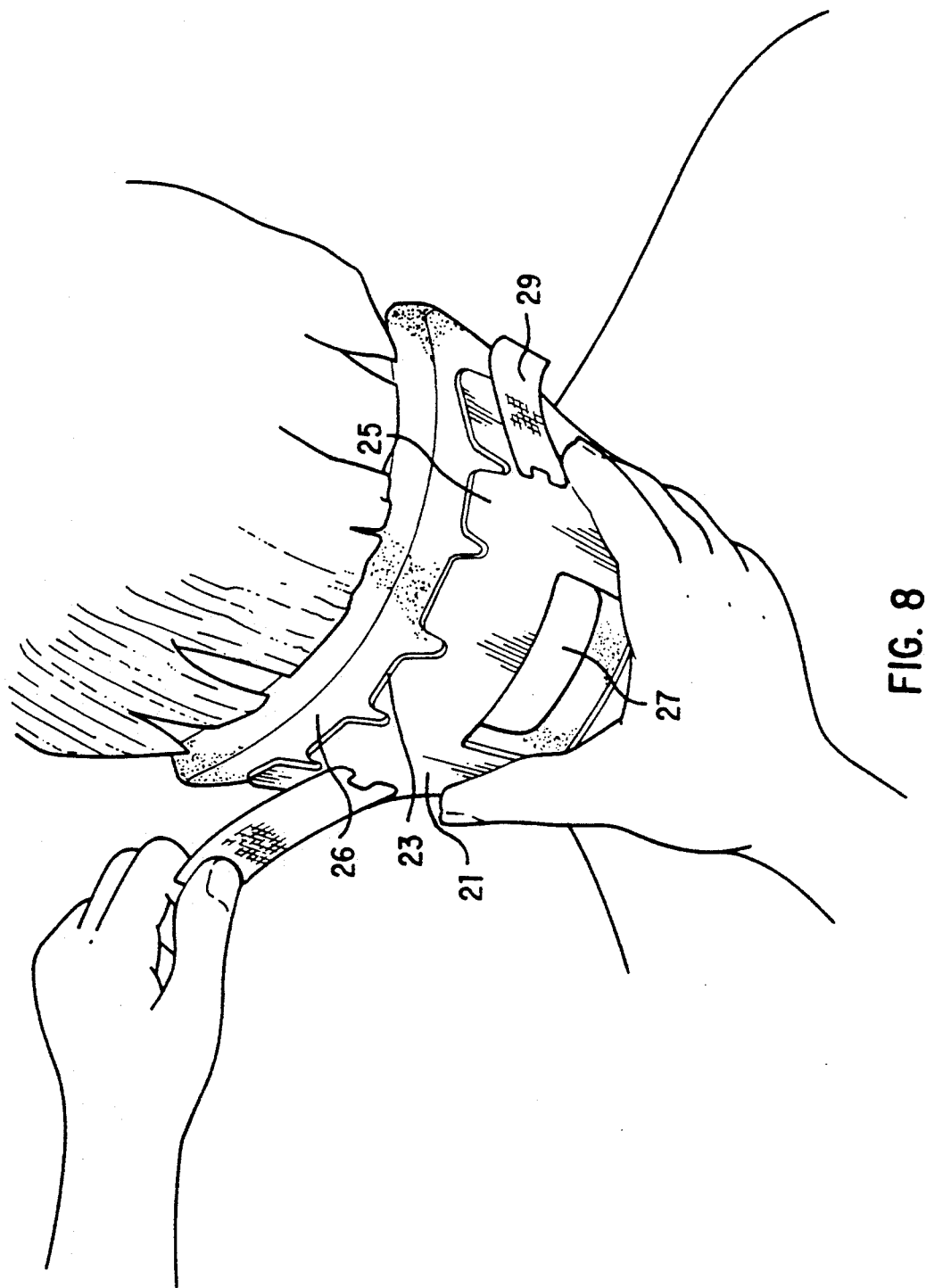
FIG. 8 depicts the application of an alternative embodiment of the present invention to a patient.

In the preferred embodiment shown in FIGS. 7-10, after the collar is applied as described above, the occiput supporting shelf is provided by flexing back portion 21 of the collar to increase its degree of curvature to conform to the patient's occiput. Strap 29 or 41 is then pulled taut as shown in FIGS. 7 and 8 such that pad 26 is pulled away from the inner surface of back portion 21 and supported in such position by strap 29 or 41. The ends of strap 29 or 41 are then secured to hold the collar in this configuration. In a alternative embodiment, pad 26 could be eliminated such that the occiput supporting shelf is formed by strap 29 or 41 alone. In alternative embodiments, the back portion of the collar and the shelf-forming pad can be conformed prior to application of the collar to the wearer.

Figure 13:
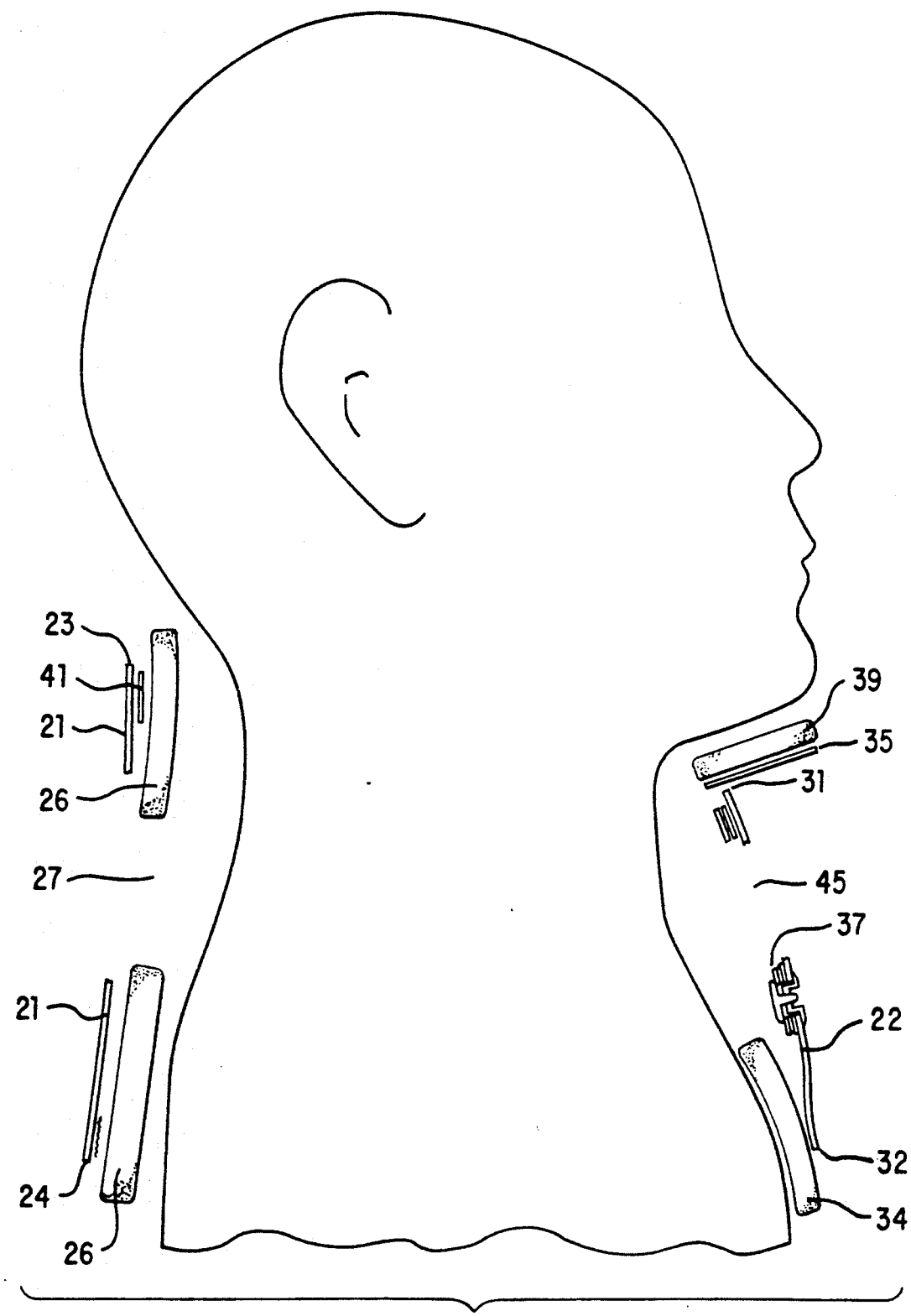
Figure 14:
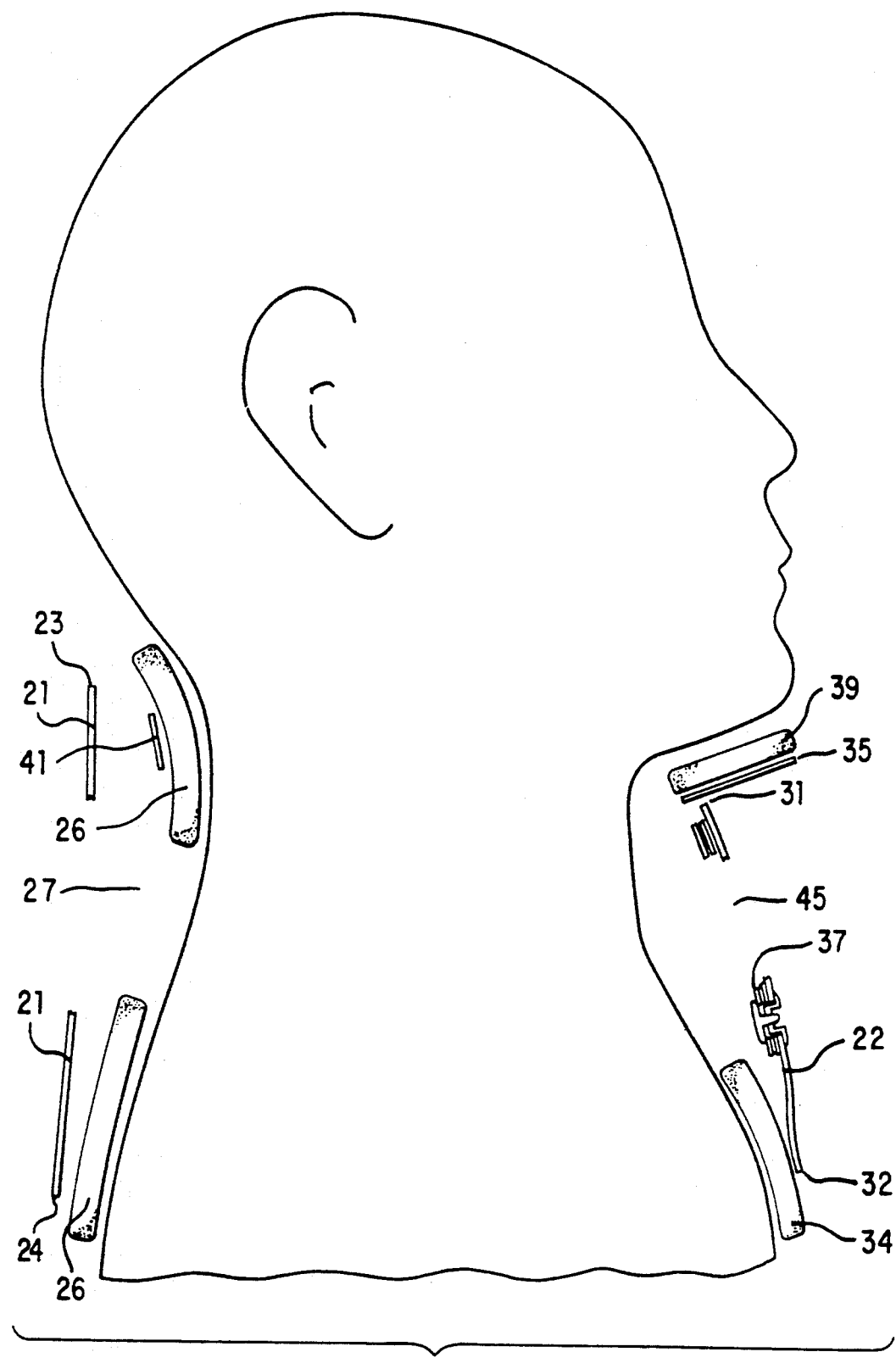

As shown by comparison of FIGS. 11 and 13 with FIGS. 12 and 14, formation of the occiput supporting shelf supports the lower occipital region of the wearer's head, resulting in greater wearer comfort. The shelf formed by this construction provides a greater point of contact which can bear some of the load presented by the patient's head (which would otherwise be carried by the posterior muscles of the neck).

Figure 15:
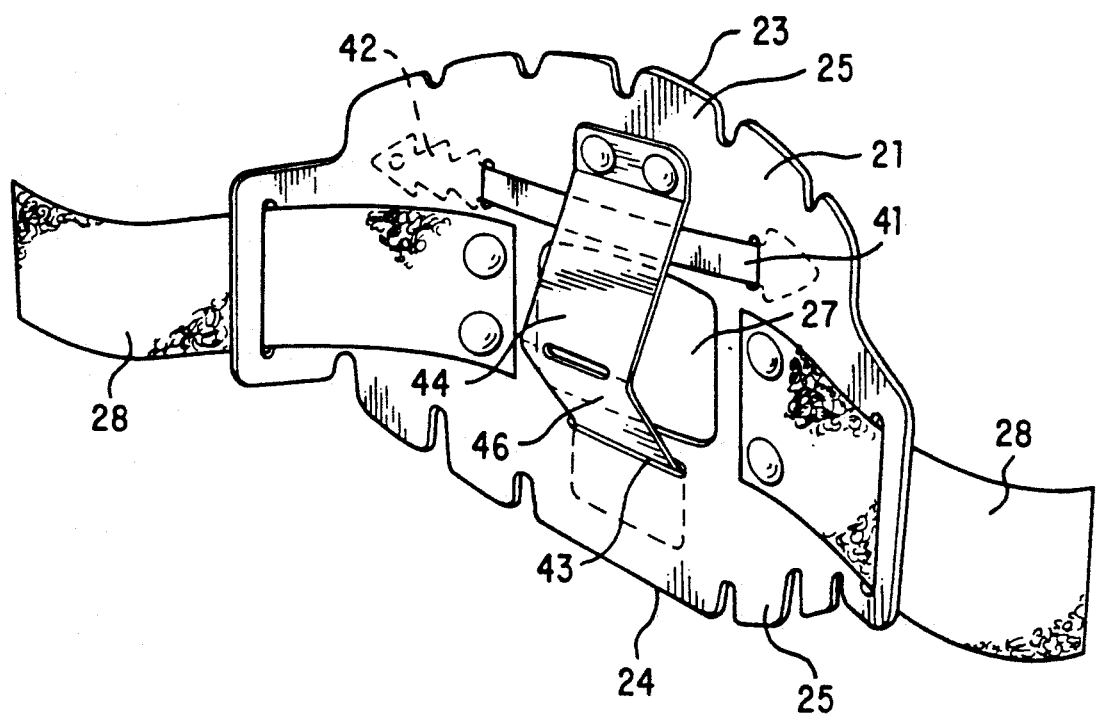
FIG. 15 is a perspective view of the back portion of an alternative embodiment of the present invention.

FIG. 15 depicts an alternative construction which provides an occiput supporting shelf in accordance with the present invention. In this embodiment no pad is employed. Instead flexible member 46 provides the supporting surface. Flexible member 46 is attached at one end to back portion 21. Its other end extends through slot 43 in back portion 21. Flexible member 46 is made of a stiff, flexible material such as those materials preferred for formation of the neck encircling band, cardboard, etc. Strap 41 operates in the manner previously described. When back portion 21 is flexed into the desired conformation surface 44 contacts the patient's occiput. The angle of surface 44 can be adjusted by moving flexible member 46 into or out of slot 43 to achieve the desired angle corresponding to the contour of patient's occiput.

Flexing back portion 21 in the manner described to form the occiput supporting shelf also results in some redistribution of the load on the chin piece. As shown by comparison of FIGS. 9 and 10, as the back portion of the collar is flexed, the diameter of the collar from the patient's left to right decreases. As a result, the chin support is also flexed such that its ends are closer together, resulting in a shift of the load toward the posterior portion of the mandible and a slight lifting of the chin from the chin support as shown by comparison of FIGS. 11 and 12.

In alternative embodiments, other means could be used to provide an occiput supporting shelf. For example, although a pad is preferred, the shelf could be formed from other materials which can be conformed to the desired shape, such as polyethylene, polyurethane, cardboard, paper, cloth, etc. Furthermore, means other than a strap o tabbed strip can be used to place the back portion of the collar in the proper conformation and to support the shelf-forming member (e.g., the pad), such as belts, cords, strings, etc.

The combined effects of load redistribution resulting from flexing the back portion of the collar and formation of the occiput supporting shelf and that provided by load-bearing construction supporting the chin support provide an especially favorable increase in wearer comfort. Embodiments employing both the occiput supporting shelf and load-bearing construction of the present invention provide upward balanced support of the head while moving the primary load-bearing points away from the underside of the patient's chin at midline.

What is claimed is:

1. A cervical collar comprising (a) a neck encircling band formed from a stiff flexible plastic material comprising a back portion and a front portion, said front portion having a substantially continuous top edge and (b) a chin support formed from a stiff flexible plastic material, wherein said chin support is supported above said top edge by a plurality of load bearing means extending upwardly from said front portion which shift the point of contact between said chin support and said front portion in response to increased force on said chin support.

2. The collar of claim 1 wherein said load bearing means are a plurality of load bearing tabs.

3. The collar of claim 1 wherein said load bearing means are a plurality of load bearing tabs extending from said top edge of said front portion.

* * * * *